United States Patent
Shinshi et al.

(10) Patent No.: US 8,596,999 B2
(45) Date of Patent: *Dec. 3, 2013

(54) DISPOSABLE CENTRIFUGAL BLOOD PUMP WITH MAGNETIC COUPLING

(75) Inventors: Tadahiko Shinshi, Kanagawa (JP); Akira Shimokohbe, Kanagawa (JP); Junichi Asama, Kanagawa (JP); Chikara Hara, Kanagawa (JP); Wataru Hijikata, Kanagawa (JP); Setsuo Takatani, Tokyo (JP); Hideo Hoshi, Tokyo (JP)

(73) Assignees: Tokyo Institute of Technology, Tokyo (JP); Tokyo Medical and Dental University, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/397,599

(22) Filed: Feb. 15, 2012

(65) Prior Publication Data

US 2012/0207630 A1 Aug. 16, 2012

Related U.S. Application Data

(63) Continuation of application No. 12/065,687, filed as application No. PCT/JP2006/317370 on Sep. 1, 2006, now Pat. No. 8,123,503.

(30) Foreign Application Priority Data

Sep. 5, 2005 (JP) .................................. 2005-256278

(51) Int. Cl.
*F04B 17/00* (2006.01)
(52) U.S. Cl.
USPC .......................................... 417/420; 415/900
(58) Field of Classification Search
USPC ................. 417/420, 423.14; 415/900; 600/17
See application file for complete search history.

(56) References Cited

U.S. PATENT DOCUMENTS

| 4,984,972 A | * | 1/1991 | Clausen et al. | ............... 417/420 |
| 5,393,207 A | * | 2/1995 | Maher et al. | ............... 417/423.7 |

(Continued)

FOREIGN PATENT DOCUMENTS

| EP | 0899857 | 3/1999 |
| JP | 3-286775 | 12/1991 |

(Continued)

OTHER PUBLICATIONS

Supplemental Search Report for European Patent Application No. 06797312.3 mailed Sep. 6, 2010.

(Continued)

*Primary Examiner* — Devon Kramer
*Assistant Examiner* — Amene Bayou
(74) *Attorney, Agent, or Firm* — Billion & Armitage; Benjamin C. Armitage

(57) ABSTRACT

A disposable centrifugal blood pump with magnetic coupling provides a centrifugal blood pump with magnetic coupling which is simple in structure of disposable parts with low cost. Therefore, a housing as the disposable part includes a rotor having pole faces extending on the outer-peripheral surface and projecting inward from the inner-peripheral surface and an impeller attached to the rotor, and a stator as a reusable part includes three or more electromagnets for electromagnetic coupling for forming a magnetic coupling between the stator and the rotor, a torque transmission disk formed by sandwiching a ring-shaped permanent magnet between two upper and lower ring members and having pole faces corresponding to the pole faces projecting from the inner-peripheral surface of the rotor formed to project for generating a magnetic coupling between stator and rotor, a motor for rotating the torque transmission disk, and a displacement gauge for measuring displacement of the rotor.

19 Claims, 8 Drawing Sheets

(56) References Cited

U.S. PATENT DOCUMENTS

| | | | |
|---|---|---|---|
| 5,947,703 A * | 9/1999 | Nojiri et al. | 417/420 |
| 6,030,188 A * | 2/2000 | Nojiri et al. | 417/420 |
| 6,053,705 A * | 4/2000 | Schob et al. | 417/53 |
| 6,155,969 A | 12/2000 | Schima et al. | |
| 6,181,040 B1 * | 1/2001 | Schob | 310/90.5 |
| 6,626,644 B2 * | 9/2003 | Ozaki | 417/45 |
| 8,123,503 B2 * | 2/2012 | Shinshi et al. | 417/420 |
| 2003/0124007 A1* | 7/2003 | Schima et al. | 417/420 |
| 2004/0143151 A1* | 7/2004 | Mori et al. | 600/16 |
| 2005/0287022 A1* | 12/2005 | Yaegashi et al. | 417/420 |

FOREIGN PATENT DOCUMENTS

| | | |
|---|---|---|
| JP | 9-206373 | 8/1997 |
| JP | 2000-502420 | 2/2000 |
| WO | WO 2006/053384 | 5/2006 |

OTHER PUBLICATIONS

"CentriMag® Left Ventricular Assist System," PL-019 Rev. 00, © 2003 Levitronix (2003), 4 pgs.

International Search Report for PCT/JP2006/317370 mailed Nov. 28, 2006.

Hoshi et al., "Magnetically suspended centrifugal blood pump with a radial magnetic driver," ASAIO Journal (2005): 60-64.

Schob, R., "Centrifugal pump without bearings or seals," World Pumps (Jul. 2002): 2-5.

Schob, R., "Fundamentals of the baringless electric motor and its applications," (2003), 24 pgs.

International Preliminary Report on Patentability and Written Opinion for PCT/JP2006/317370 mailed Mar. 20, 2008.

* cited by examiner

DISPOSABLE CENTRIFUGAL BLOOD PUMP WITH MAGNETIC COUPLING

CROSS-REFERENCE TO RELATED APPLICATION

This application is a continuation of U.S. patent application Ser. No. 12/065,687, filed Nov. 5, 2009, now U.S. Pat. No. 8,123,503 scheduled to issue on Feb. 28, 2012, which is a U.S. National Stage application claiming benefit of prior filed International Application PCT/JP2006/317370, filed Sep. 1, 2006, in which the International Application claims a priority date of Sep. 5, 2005 based on prior filed Japanese Patent Application No. 2005-256278, the entire contents of which are incorporated herein by reference.

TECHNICAL FIELD

The present invention relates to a centrifugal blood pump in which only blood-contact parts are disposable parts and, more specifically, to a disposable centrifugal blood pump with magnetic coupling employing a magnetic coupling rotor which is simple in structure of the disposable parts, has a small number of permanent magnets, is low cost, and is easy to manufacture.

BACKGROUND ART

In the related art, as a centrifugal blood pump used during cardiac surgery or after cardiac surgery, a disposable centrifugal blood pump in which only an impeller (vane wheel) which comes into contact with blood of a patient and a housing (pump housing) for storing the same are replaced is used.

Normally, in the disposable centrifugal blood pump of this type, the impeller is supported by a pivot bearing or a contact bearing protected by a mechanical seal. However, since the bearing is used without lubrication in order to avoid contamination of blood, it is subjected to intensive abrasion or friction, which leads to a problem of durability. There are also problems being pointed out such as plaque formation around the bearing or hemolysis caused by the bearing.

Therefore, the expiration date for use of these disposable parts is limited to about two days at maximum. However, replacement which has to be done every two days is actually heavy burden for patients and medical institution that need long-term auxiliary circulation.

In order to solve such problems, a disposable centrifugal blood pump with magnetic coupling employing a magnetic coupling which supports an impeller to be integrated in a centrifugal blood pump with a magnetic force in a non-contact manner has been proposed (see Non-Patent Documents 1 to 3).

The disposable centrifugal blood pumps with magnetic coupling disclosed in Non-Patent Documents 1 and 2 employ a cylindrical permanent magnet magnetized in the radial direction used as a rotor in the housing as in the case of a brushless DC motor, and the disposable centrifugal blood pump with magnetic coupling disclosed in Non-Patent Document 3 is configured in such a manner that the rotor is supported by magnetic coupling working between an electromagnet provided on the side of a stator around the outer periphery of the rotor and a permanent magnet provided on the rotor, and torque is transmitted to the rotor by magnetic coupling working between a plurality of permanent magnets provided on the inner surface of the rotor and a plurality of permanent magnets of a torque transmission disk disposed so as to oppose the permanent magnets.

Non-Patent Document 1: Reto Schob, Centrifugal pump without bearings or seals, World Pumps, July 2002.
Non-Patent Document 2: CentriMag Left Ventricular Assist System Catalogue, Levitronix.
Non-Patent Document 3: H. Hoshi, K. Kataoka, K. Ohuchi, J. Asama, T. Shinshi, A. Shimokohbe and S. Takatani, Magnetically Suspended Blood Pump with a Radial Magnetic Driver, ASAIO journal, pp. 60-64, (2005).

DISCLOSURE

Problems to be Solved

However, in the related arts disclosed in Non-Patent Documents 1 and 2, the permanent magnet occupies a high ratio in a magnetic circuit, and hence it is supposed that magnetic resistance becomes large.

When the magnetic resistance is large as described above, a large amount of coil current for a motor and magnetic suspension is necessary. Therefore, it is supposed that there arises a problem of heat generation.

When the plurality of permanent magnets are used for the rotor as in Non-Patent Document 3, there are problems such that the structure of the rotor is complicated and hence the manufacturing cost is increased, and that it takes a lot of trouble to secure reliability by preventing separation of the permanent magnet due to incomplete adhesion.

In view of such circumstances, it is an object of the present invention to provide a disposable centrifugal blood pump with magnetic coupling employing a magnetic coupling rotor having a disposable part in simple structure, having small number and ratio of permanent magnets in a magnetic circuit, generating small amount of heat, and being manufactured with ease at a low cost.

Means for Solving the Problems

In order to achieve the object described above, the centrifugal blood pump stated in Claim 1 includes a disposable housing provided with an inflow on top thereof and an outflow on a side surface thereof, and a stator as a reusable part to which the housing is detachably attached, and is characterized in that the housing includes in the interior thereof a cylindrical rotor being formed of magnetic material and having ring-shaped pole faces extending along the circumferential direction on one side and the other side of the outer peripheral surface thereof so as to project therefrom and having a plurality of pole faces projecting inward from the inner peripheral surface thereof on the one side and the other side and an impeller attached to the rotor, the stator includes three or more electromagnets for electromagnetic coupling being arranged around the housing at regular intervals and having pole faces opposed to the pole faces projected from the outer peripheral surface of the rotor, the electromagnets generating a magnetic coupling between the stator and the rotor, a torque transmission disk formed by sandwiching a ring-shaped permanent magnet magnetized in the direction of thickness between two upper and lower ring members formed of magnetic material and having a plurality of pole faces corresponding to the pole faces projecting from the inner peripheral surface of the rotor formed so as to project therefrom on one side and the other side of the outer peripheral surface thereof for generating a magnetic coupling between the stator and the rotor, a motor arranged apart from the housing for rotating the torque transmission disk, and a displacement gauge for measuring displacement of the rotor in the radial direction, and the housing has a bottom formed into a cylindrical shape along the contour shape of the rotor and detachably attached between the electromagnets for electromagnetic coupling and the torque transmission disk.

The invention stated in Claim 2 is the disposable centrifugal blood pump with magnetic coupling according to Claim 1, wherein the rotor is formed by sandwiching one ring-shaped permanent magnet magnetized in the direction of thickness between two upper and lower ring members formed of magnetic material and formed with teeth in the axial direction on the inner peripheral side thereof, and the permanent magnet of the torque transmission disk is magnetized in the direction opposite from the permanent magnet of the rotor.

The invention stated in Claim 3 is the disposable centrifugal blood pump with magnetic coupling according to Claim 1 or 2, wherein the housing is fixed to the stator via a fixing device.

The invention stated in Claim 4 includes a disposable housing provided with an inflow on top thereof and an outflow on a side surface thereof, and a stator as a reusable part to which the housing is detachably attached, and is characterized in that the housing includes in the interior thereof a cylindrical rotor being formed of magnetic material and having ring-shaped pole faces extending along the circumferential direction on one side and the other side of the outer peripheral surface thereof so as to project therefrom and having a plurality of pole faces projecting in the axial direction formed on the inner peripheral surface thereof and an impeller attached to the rotor, the stator includes three or more electromagnets for electromagnetic coupling being arranged around the housing at regular intervals and having pole faces opposed to the pole faces projected from the outer peripheral surface of the rotor, the electromagnets generating a magnetic coupling between a torque transmission disk and the rotor, and between the electromagnets for electromagnetic coupling and the rotor, a torque transmission disk configured of a Halbach type permanent magnet array including a row of permanent magnets whose directions of magnetization are shifted by 90° for generating a magnetic coupling between the stator and the pole faces formed on the inner peripheral surface side of the rotor so as to oppose the permanent magnets magnetized inwardly and outwardly in the radial direction, a motor arranged apart from the housing for rotating the torque transmission disk, and a displacement gauge for measuring displacement of the rotor in the radial direction, and the housing has a bottom formed into a cylindrical shape along the contour shape of the rotor and detachably attached between the electromagnets for electromagnetic coupling and the torque transmission disk.

The invention stated in Claim 5 is the disposable centrifugal blood pump with magnetic coupling according to Claim 4, wherein the housing is fixed to the state via a fixing device.

Effect of the Invention

According to the invention stated in Claim 1, Claim 2 and Claim 4, since the number of the permanent magnets used for the rotor in the housing as the disposable part may be dramatically reduced in comparison with the related art, a simple rotor structure is achieved, which advantageously contributes to reduction of cost for the disposable part.

The magnetic resistance of the magnetic circuit is small, which is advantageous for reduction of power consumption of the magnetic coupling.

Furthermore, with the structure in which the motor is positioned apart from the housing so that heat of the motor is prevented from being transferred easily to blood flowing down in the housing, coagulation of blood due to heat is reliably prevented.

According to the invention stated in Claim 3 and Claim 5, the housing as the disposable part is fixed with the fixing device, the possibility of occurrence of unexpected accident such as coming off of the housing when it is used during cardiac surgery or after the cardiac surgery is avoided.

DETAILED DESCRIPTION OF THE EMBODIMENTS

Hereinafter, embodiments of the present invention will be described in detail on the basis of the drawings.

Figure 1:
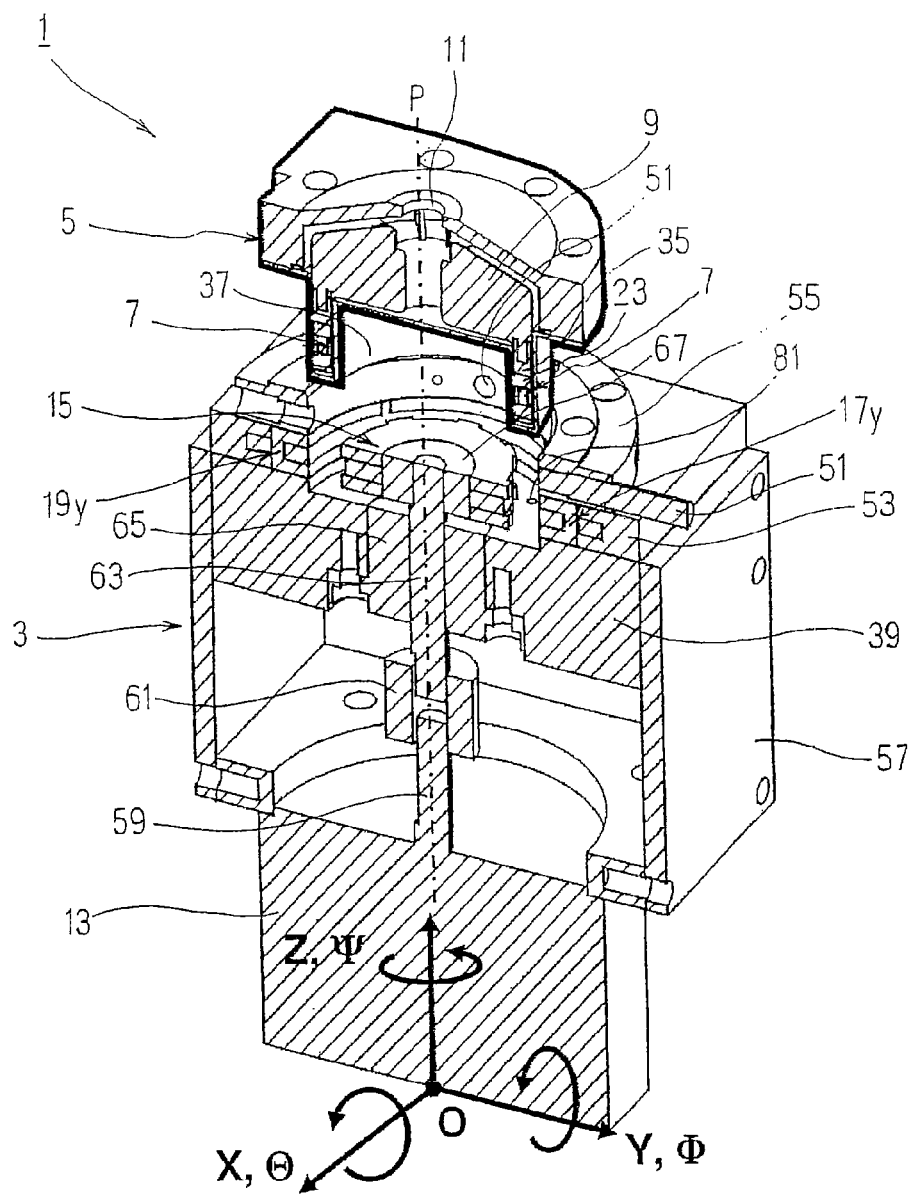
FIG. 1 is a perspective cross-sectional view of an entire disposable centrifugal blood pump with magnetic coupling according to a first embodiment described in Claim 1 to Claim 3.

FIG. 1 to FIG. 6 illustrate a first embodiment of a disposable centrifugal blood pump with magnetic coupling (hereinafter referred to as "centrifugal blood pump with magnetic coupling") according to Claim 1 to Claim 3. As shown in FIG. 1, a centrifugal blood pump with magnetic coupling 1 according to this embodiment includes a stator 3 and a housing 5 which is detachably attached to the upper surface of the stator 3 and, as described below, a blood-contact part including the housing 5, a rotor 7, an impeller 9, and so on mounted to the interior thereof and being surrounded by a thick line in the drawing corresponds to a disposable part, and blood flowed from an inflow 11 on top of the housing 5 is provided with kinetic energy by the rotation of the impeller 9 and flowed out from an outflow (not shown) on a side surface thereof.

Then, the stator 3 including a brushless DC motor (hereinafter referred to as "motor") 13 arranged apart from the housing 5, a torque transmission disk 15 rotating synchronously therewith, and four electromagnets 17$x$, 19$x$, 17$y$, 19$y$ for magnetic coupling shown in FIG. 3 arranged so as to surround the periphery of the housing 5 corresponds to a reusable part of the centrifugal blood pump with magnetic coupling 1. The housing 5 is set to have an outer diameter of 75 mm, and the stator 3 as the reusable part is set to have a height of 157 mm.

Figure 2:
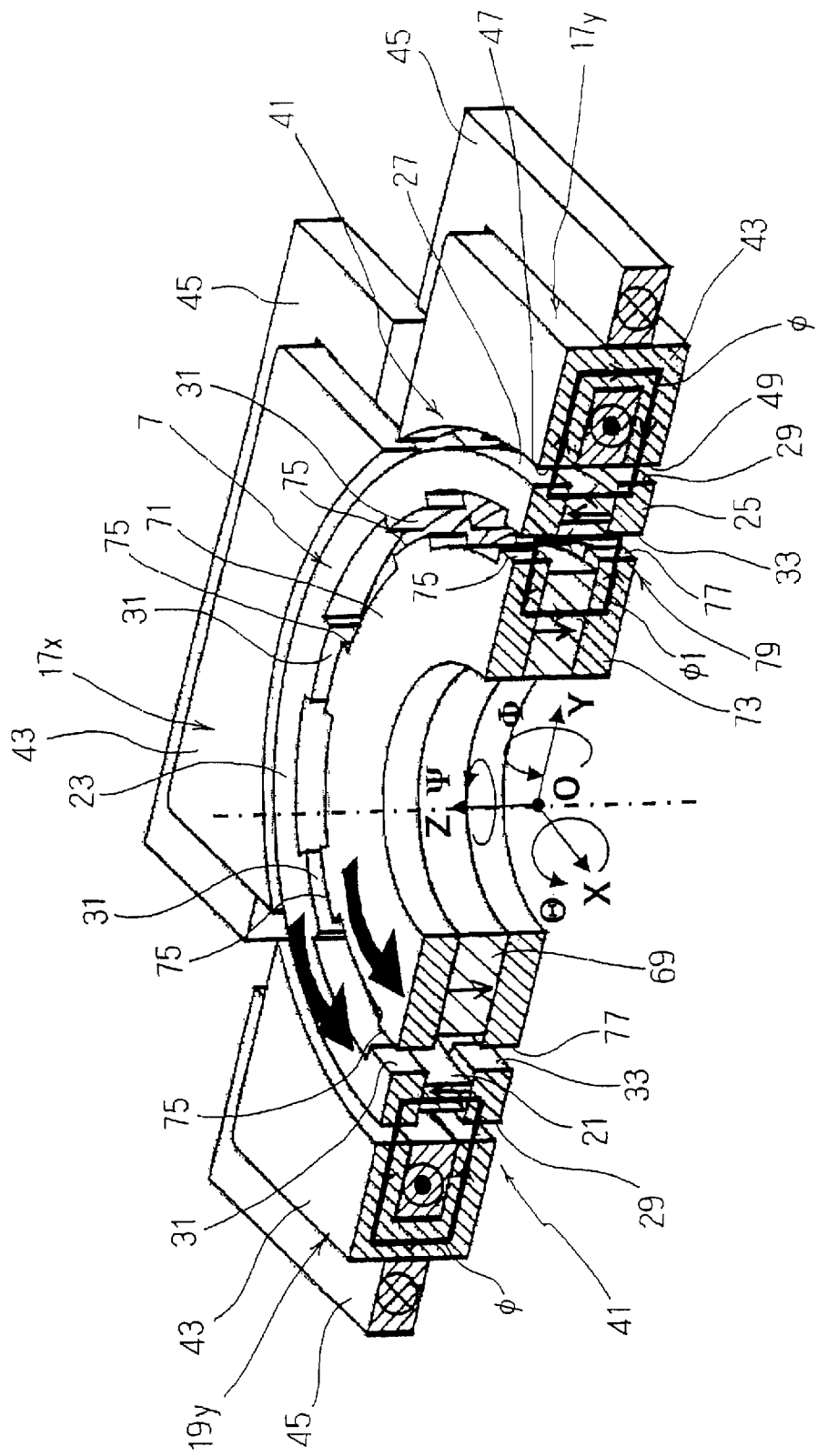
FIG. 2 is an enlarged perspective cross-sectional view of a rotor, an electromagnet and a torque transmission disk of the disposable centrifugal blood pump with magnetic coupling shown in FIG. 1.

The disposable part including the housing 5 and the rotor 7 and the impeller 9 mounted in the interior thereof will now be described. In FIG. 2, reference numeral 21 designates a ring-shaped neodymium permanent magnet magnetized in the direction of the thickness thereof, and reference numerals 23, 25 designate two magnetic soft iron rings (ring members) each having the inner peripheral surface formed with teeth in the axial direction at regular intervals, and the neodymium permanent magnet 21 is sandwiched integrally between the magnetic soft iron rings 23, 25 to form the rotor 7.

The outer peripheral surface of the magnetic soft iron ring 23, that is, one end side of the outer peripheral surface of the rotor 7 projects outward from the neodymium permanent magnet 21 and defines a ring-shaped pole face 27 formed along the circumferential direction. In the same manner, the outer peripheral surface of the magnetic soft iron ring 25, that is, the other end of the outer peripheral surface of the rotor 7 also projects outward from the neodymium permanent magnet 21 and defines a ring-shaped pole face 29 formed along the circumferential direction. A stationary magnetized direction is generated between the two pole faces 27, 29 by the neodymium permanent magnet 21.

Figure 4:
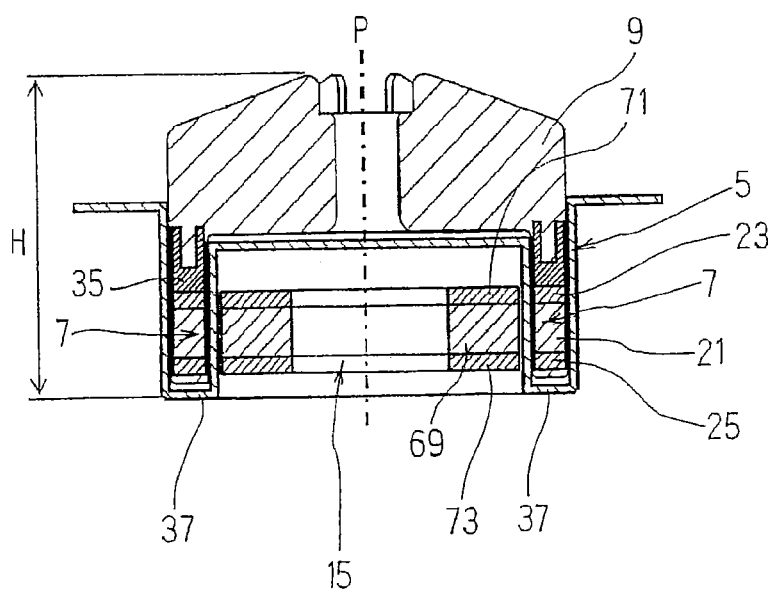
FIG. 4 is a vertical cross-sectional view of a housing.

As described above, the inner peripheral surfaces of the magnetic soft iron rings 23, 25 are formed respectively with teeth in the axial direction at regular intervals, whereby a plurality of teeth-like pole faces 31, 33 are formed at the same positions on the one end and the other end of the inner peripheral surface of the rotor 7 so as to project inward at regular intervals. As shown in FIG. 1 and FIG. 4, the impeller 9 formed of resin material such as acryl is integrally secured to the rotor 7 (magnetic soft iron ring 23) via a connecting member (a sensor target of a displacement sensor described later) 35, and the rotor 7 and the impeller 9 are stored in the housing 5.

The housing 5 is formed of light resin material like the impeller 9, and is formed with the inflow 11 and the outflow on the top and the side surface of the housing 5 as described above, and as shown in FIG. 4, a bottom 37 is formed into a cylindrical shape along the contour shape of the rotor 7.

Figure 7:
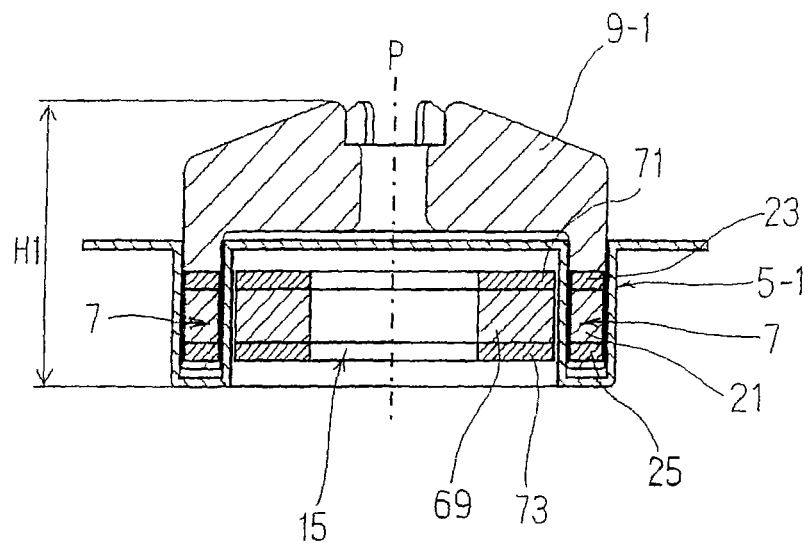
FIG. 7 is a vertical cross-sectional view of a modification of the housing.

As shown in FIG. 4, in this embodiment, a height H from the bottom 37 of the housing 5 to the top of the impeller 9 is set to approximately 39.5 mm. However, as shown in FIG. 7, by removing the connecting member (sensor target) 35 and securing an impeller 9-1 which is smaller in height directly to the rotor 7 (magnetic soft iron ring 23), the disposable part including a housing 5-1, the rotor 7 and the impeller 9-1 is downsized. In this case, the neodymium permanent magnet 21 of the rotor 7 is used as the sensor target of the displacement sensor.

As described above, in this embodiment, the plurality of teeth-like pole faces 31, 33 are formed on the inner peripheral surfaces of the magnetic soft iron rings 23, 25 so as to project inward at regular intervals. However, these pole faces 31, 33 do not necessarily have to be arranged at regular intervals. For example, four pole faces 31, 33 may be formed at intervals of 100° and 80° respectively in line symmetry so as to project therefrom.

Figure 3:
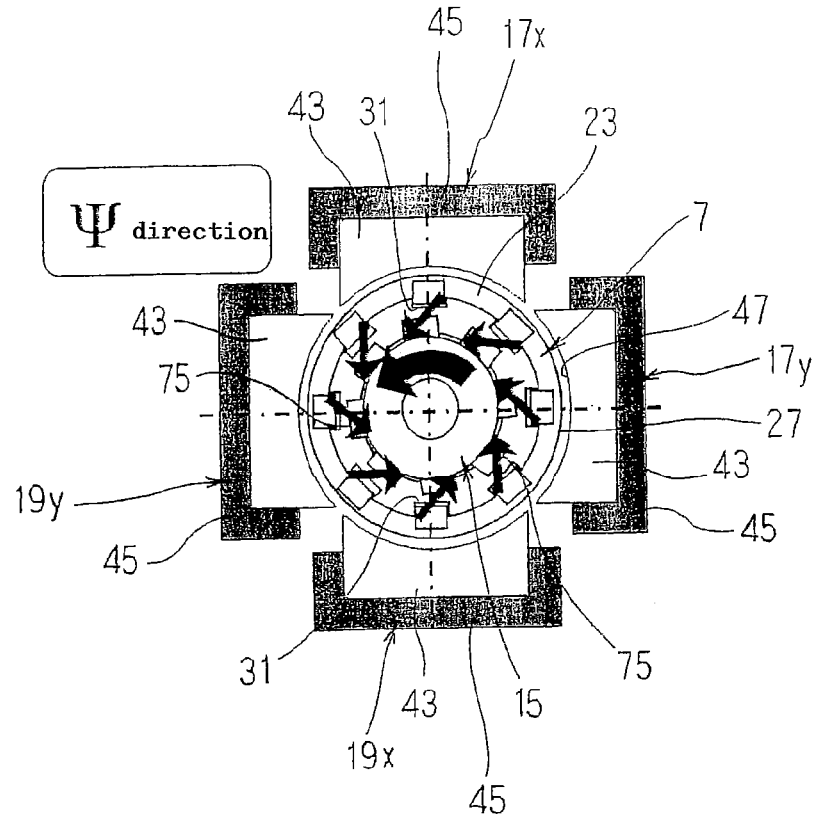
FIG. 3 is a plan view of the rotor, the electromagnet and the torque transmission disk.

As shown in FIG. 1 to FIG. 3, the four electromagnets 17x, 19x, 17y, 19y are arranged at intervals of 90° on a base 39 so as to surround the bottom 37 of the rotor 7 arranged on the base 39 of the stator 3, and the electromagnets 17x, 19x, 17y, 19y and the rotor 7 configure a magnetic coupling 41 which supports the load of the impeller 9 by a magnetic force in non-contact manner.

As shown in FIG. 2, the magnetic coupling 41 is a coupling having positive rigidity in five degrees of freedom except for the direction of rotation (direction Ψ) about the direction of thrust of the impeller 9 (direction Z).

The five degrees of freedom correspond to one degree of freedom in the direction of thrust (direction Z), two degrees of freedom in the radial directions (direction X and direction Y), and two degrees of freedom in the directions of inclination (direction Θ and direction Φ). The direction of thrust corresponds to the direction of the rotational axis of the impeller 9, the radial direction corresponds to a direction vertical to the direction of the rotational axis, and the direction of inclination corresponds to the direction of minute rotation about the radial direction.

Furthermore, the magnetic coupling 41 is a magnetic coupling of two-degrees-of-freedom-controlled type, and only two degrees of freedom from among five degrees of freedom described above, that is, the two degrees of freedom of the radial directions (direction X, direction Y) are controlled. In other words, only the radial directions (direction X, direction Y) are positively controlled and other three degrees of freedom of the direction of thrust (direction Z) and the direction of inclination (direction Θ and direction Φ) are passively controlled.

Hereinafter, the configuration of the magnetic coupling 41 will be described. As shown in FIG. 2 and FIG. 3, the electromagnets 17x, 19x, 17y, 19y include the two electromagnets 17x, 19x for x-direction control, and two electromagnets 17y, 19y for y-direction control, and the electromagnets 17x, 19x for x-direction control are arranged so as to oppose to each other in the x-direction with the intermediary of the rotor 7 (the bottom 37 of the housing 5) and the electromagnets 17y, 19y for y-direction control are arranged so as to oppose to each other in the y-direction also with the intermediary of the rotor 7.

Since the configurations of the electromagnets 17x, 19x, 17y, 19y are all the same, the electromagnet 17y will be described as an example on the basis of FIG. 2 and FIG. 5. The electromagnet 17y is formed by winding a coil 45 at the center of a magnetic soft iron core 43 of an angular C-shape in cross section. When the magnetic soft iron core 43 is formed of annealed pure iron, hysteresis loss of the magnetic coupling 41 is lowered, which contributes to reduction of possibility of heat generation of the electromagnet 17y, so that coagulation of blood flowing down in the housing 5 is prevented.

When the magnetic soft iron core 43 is formed of powder core (fine particles of pure iron which are compressed and bound with adhesive agent), eddy current loss is reduced, which contributes to reduction of possibility of heat generation of the electromagnet 17y and allows the band width of the electromagnetic force emitted from and controlled by the magnetic coupling 41 to be expanded, so that the vibrations of the rotor 7 are advantageously reduced, which contributes to prevention of hemolysis or prevention of coagulation of blood.

The magnetic soft iron core 43 is provided with two pole faces 47, 49 arranged so as to oppose respective partial areas of the pole faces 27, 29 of the rotor 7 and, as shown in FIG. 2 and FIG. 3, the shapes of the pole faces 47, 49 extend along the partial areas of the pole faces 27, 29 of the rotor 7. Then, the gap between the pole faces 27, 29 and the pole faces 47, 49, which oppose to each other with the intermediary of the bottom 37, is set to a silver-thin margin.

In this manner, the rotor 7 and the electromagnet 17y are arranged in such a manner that the pole faces 27 and 47 are arranged so as to oppose to each other and the pole faces 29, 49 are arranged so as to oppose to each other. Therefore, the stationary magnetized direction generated between the pole faces 27, 29 by the neodymium permanent magnet 21 of the rotor 7 passes through the interior via the pole faces 47, 49 of the electromagnet 17y.

Figure 5:
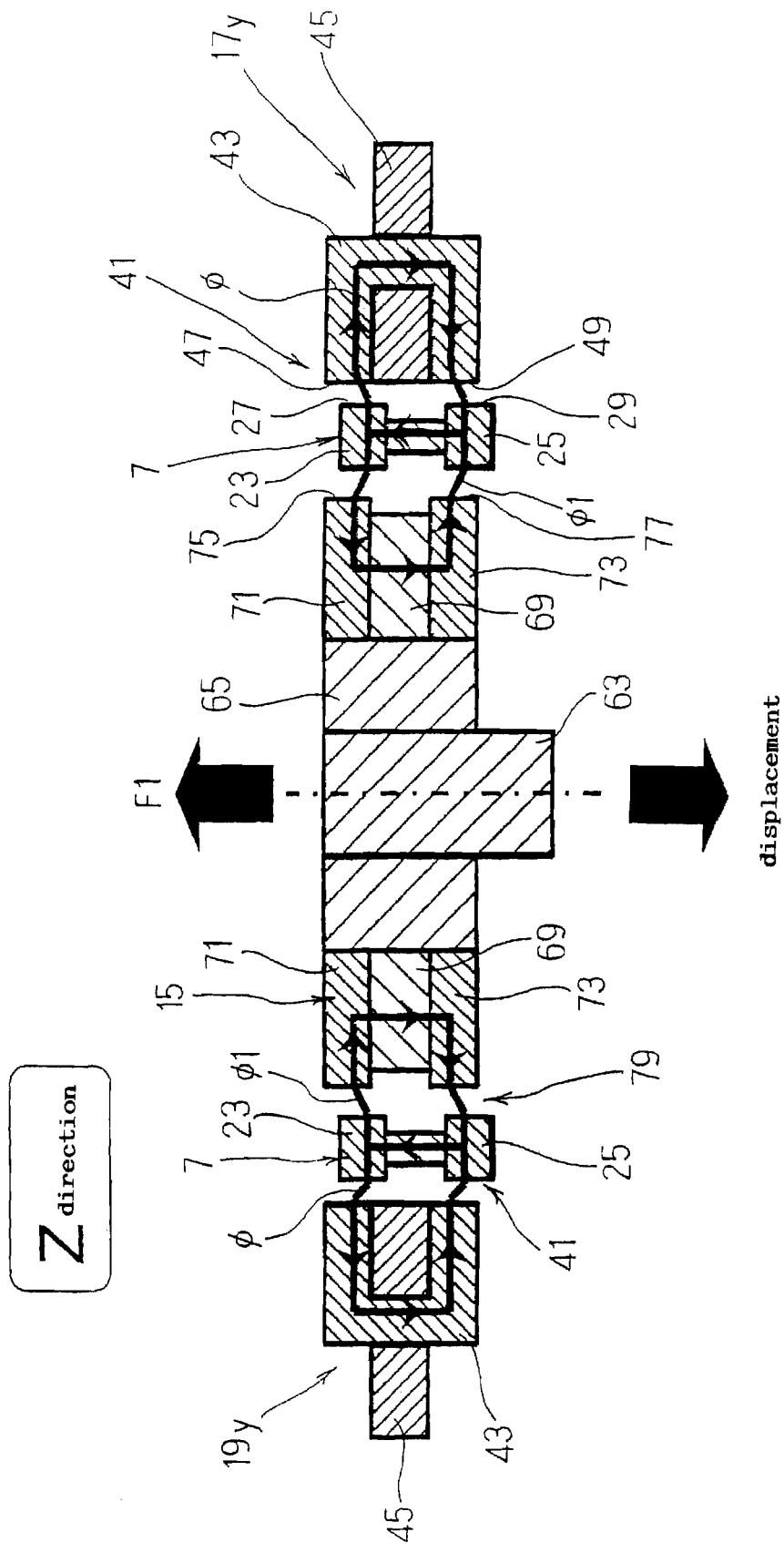
FIG. 5 is a vertical cross-sectional view of the rotor, the electromagnet and the torque transmission disk.

In other words, a magnetic coupling which forms a closed loop with a magnetic flux φ starting from the N-pole side of the neodymium permanent magnet 21 passing through the magnetic soft iron ring 23, the pole face 27, the gap, the pole face 47, magnetic soft iron core 43, the pole face 49, the gap, the pole face 29 and the magnetic soft iron ring 25 in sequence, and then returning to the S-pole of the neodymium permanent magnet 21 as indicated by arrows in FIG. 2 and FIG. 5 is generated.

Here, the sign of rigidity of the virtual magnetic coupling is "positive" in terms of three degrees of freedom which is a combination of the direction of thrust (direction Z) and the directions of inclination (direction Θ, direction Φ). In other words, when the rotor 7 is displaced from an ideal position in one degree of freedom in the direction of thrust (direction Z) as shown in FIG. 5, a restoring force F1 by the loop of the magnetic flux φ is applied to the rotor 7.

Figure 6:
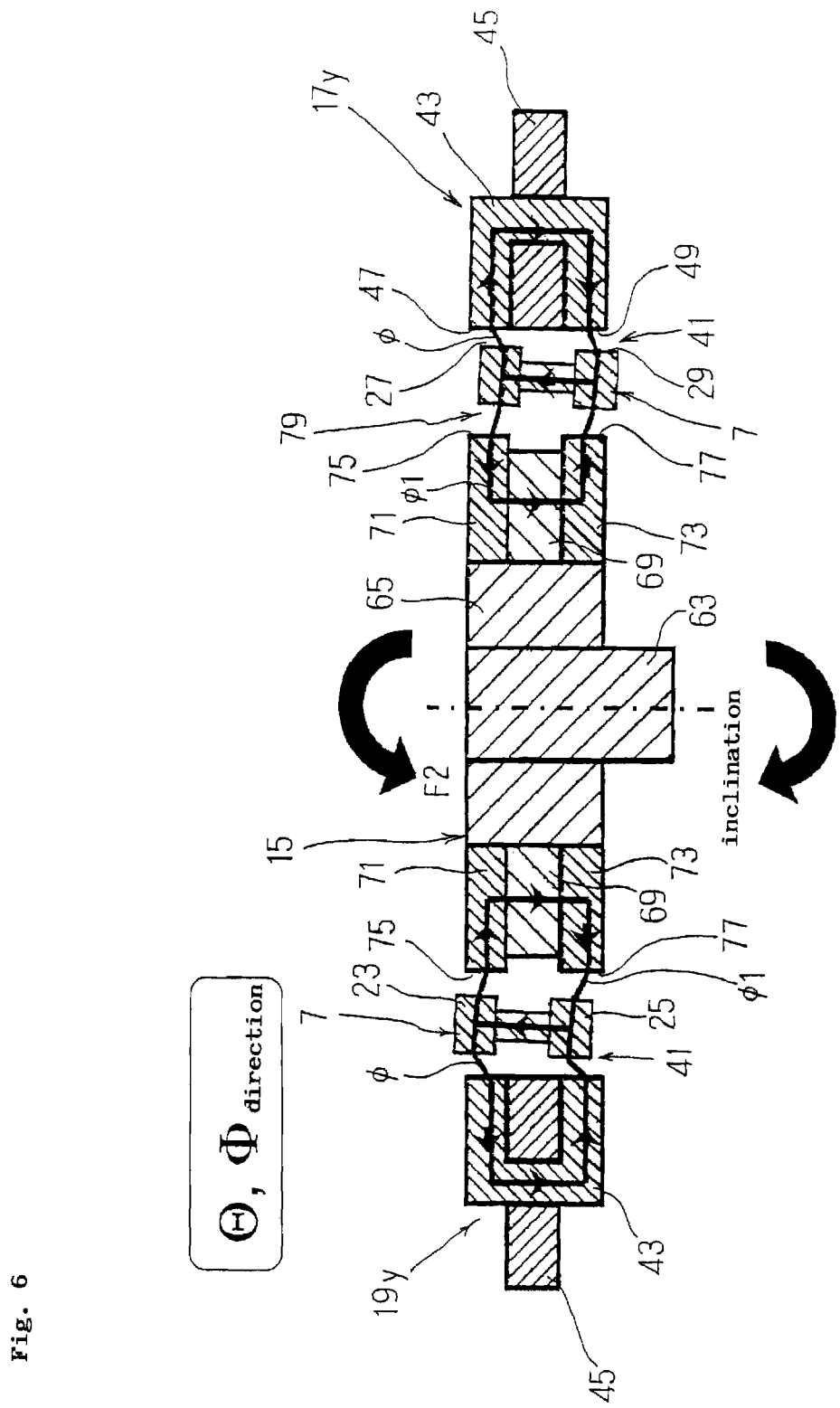
FIG. 6 is a vertical cross-sectional view of the rotor, the electromagnet and the torque transmission disk.

When the rotor 7 is inclined from the ideal position in the two degrees of freedom in the directions of inclination (direction Θ, direction Φ) as shown in FIG. 6, a restoring torque F2 by the loop of the magnetic flux φ is applied to the rotor 7.

In either cases, the rotor 7 is moved toward a state in which the pole face 27 opposes the pole face 47 of the electromagnet 17y, and the pole face 29 opposes the pole face 49 of the electromagnet 17y as shown in FIG. 2 by the restoring force F1 or the restoring torque F2 (that is, a state of being arranged in ideal positions).

The restoring force F1 or the restoring torque F2 act on the rotor 7 also in other electromagnets 17x, 19x, 19y as well.

Consequently, the rotor 7 is held stably in an arranged state in which the pole faces 27, 29 respectively oppose the pole faces 47, 49. In other words, the rigidity of the rotor 7 is sufficiently secured by the loop of the magnetic flux φ from the neodymium permanent magnet 21 as regards the three degrees of freedom in the non-control direction, which is a combination of the direction of thrust (direction Z) and the directions of inclination (direction Θ, direction Φ).

In contrast, the rigidity of a virtual spring by the loop of the magnetic flux φ from the neodymium permanent magnet 21 becomes "negative" as regards two degrees of freedom in the radial directions (direction X, direction Y).

Therefore, an exciting current is supplied to the coils 45 of the electromagnets 17x, 19x for x-direction control and electromagnets 17y, 19y for y-direction control in order to correct the rigidity of the magnetic coupling in the radial directions (direction X, direction Y) to achieve "positive" rigidity in this embodiment.

Then, the direction and strength of the exciting current with respect to the respective coils 45 are feedback-controlled on the basis of output signals from a displacement sensor 51.

As shown in FIG. 1, arranged on the base 39 of the stator 3 is an electromagnet mounting base 53 for mounting the respective electromagnets 17x, 19x, 17y, 19y on the base 39, and arranged further thereon is an annular-shaped housing mounting base 55. The two displacement sensors 51 are provided toward the center of the rotor 7 at an angular interval of 90° on the housing mounting base 55 corresponding to the electromagnets 17x, 17y, so that the displacement sensors 51 measure displacement of the rotor 7 in the radial directions (direction X, direction Y), more specifically, displacement of the connecting member (sensor target) 35 described above.

A control device for the magnetic coupling 41 compares the output signals from the displacement sensors 51 and a target position signal in the radial direction of the rotor 7 and feedback-controls to return the rotor 7 to a target position.

For example, when the rotor 7 is displaced from the ideal position in one degree of freedom in the direction X, although not shown, the control device feedback-controls the direction and the strength of the exciting current to be supplied to the coil 45 of the electromagnets 17x, 19x for x-direction control in order to generate a control force in the opposite direction from the direction of displacement.

Therefore, assuming that the rotor 7 is displaced toward the electromagnet 17x, magnetic flux in the direction opposite from the magnetic flux φ is generated by the electromagnet 17x, and magnetic flux in the same direction as the magnetic flux φ is generated by the other electromagnet 19x. At this time, the magnetic flux φ is weakened in the magnetic circuit including the magnetic soft iron core 43 of the electromagnet 17x, and the magnetic flux φ is strengthened in the magnetic circuit including the magnetic soft iron core 43 of the electromagnet 19x.

Consequently, a control force to pull back the rotor 7 toward the electromagnet 19x is generated.

Therefore, the rotor 7 is stably held at the target position so that the gap on the side of the rotor 7 and the electromagnet 19x is equal to the gap on the side of the electromagnet 17x.

Then, the same feedback control is carried out for the electromagnets 17y, 19y for y-direction control, so that the rotor 7 is stably held at the target position where the gap on the electromagnet 17y side and the gap on the electromagnet 19y side are equalized.

In other words, by the combination of the loop of the magnetic flux φ from the neodymium permanent magnet 21 and the loop of the magnetic flux from the electromagnets 17x, 19x, 17y, 19y, the rigidity of the virtual spring becomes "positive" as regards two degrees of freedom in the radial directions (direction X, direction Y) so that the rigidity of the rotor 7 is sufficiently secured.

In this manner, according to the magnetic coupling 41 of this embodiment, the sufficient rigidity is secured by the loop of the magnetic flux φ from the neodymium permanent magnet 21 as regards three degrees of freedom in the non-control direction, which is a combination of the direction of thrust (direction Z) and the directions of inclination (direction Θ, direction Φ) of the rotor 7, and the sufficient rigidity is further secured by the combination with the loop of the magnetic flux from the electromagnets 17x, 19x, 17y, 19y as regards two degrees of freedom in the radial directions (direction X, direction Y). In other words, the high rigidity is achieved in five degrees of freedom.

Furthermore, as the magnetic coupling 41 uses the electromagnets and the permanent magnet of two-degrees-of-freedom-controlled type, downsizing and reduction of power consumption are also achieved.

On the other hand, as shown in FIG. 1, provided under the stator 3 is the motor 13 so as to be apart from the housing 5 via a motor mounting frame 57 secured to the base 39, and a motor axis 59 has the same center axis P as the bottom 37 of the housing 5 which is attached to the upper surface of the stator 3 (base 39).

Then, a power transmitting shaft 63 formed of a material having low heat conductivity is connected to the motor axis 59 via a coupling 61, and the power transmitting shaft 63 is rotatably supported by the base 39 via a bearing 65. Then, the ring-shaped torque transmission disk 15 for transmitting torque to the rotor 7 is connected to the distal end of the power transmitting shaft 63 which projects from the upper surface of the base 39 via a connecting member 67 which is circular in plan view, and when the housing 5 is arranged on the upper surface of the stator 3 (base 39), the torque transmission disk 15 is arranged inside thereof so as to have the same center axis P as the bottom 37 of the housing 5 as shown in FIG. 4.

The torque transmission disk 15 has a structure in which one ring-shaped neodymium permanent magnet 69 magnetized in the opposite direction from the neodymium permanent magnet 21 of the rotor 7 is sandwiched between two upper and lower magnetic soft iron rings (ring members) 71, 73 formed with teeth on the outer peripheral surface in the axial direction at regular intervals as shown in FIG. 2 and FIG. 5.

Then, formation of the teeth on the magnetic soft iron rings 71, 73 are matched with formation of the teeth on the inner peripheral surfaces of the magnetic soft iron rings 23, 25, whereby a plurality of teeth-like pole faces 75, 77 opposing the pole faces 31, 33 of the rotor 7 are formed on the one end side and the other end side of the outer peripheral surface of the torque transmission disk 15.

Therefore, in the case of the torque transmission disk 15 as well, a magnetic coupling which forms a closed loop of magnetic flux φ1 indicated by an arrow is generated between the rotor 7 and the torque transmission disk 15 with a stationary magnetized direction between the pole faces 75, 77 generated by the neodymium permanent magnet 69 and a stationary magnetized direction between the pole faces 31, 33 generated by the neodymium permanent magnet 21 of the rotor 7 as shown in FIG. 2.

In this manner, this magnetic coupling functions between the torque transmission disk 15 and the rotor 7 as a magnetic coupling 79 which transmits torque from the motor 13 to the rotor 7 and restores displacement or inclination of the rotor 7 in the direction of thrust (direction Z) and the directions of inclination (direction Θ, direction Φ) in cooperation with the magnetic coupling 41 generated by the magnetic coupling generated between the rotor 7 and the electromagnets 17x, 19x, 17y, 19y.

As shown in FIG. 1, the housing 5 is placed on the housing mounting base 55 and the bottom 37 is inserted between the housing mounting base 55 and the torque transmission disk 15. The upper surface of the base 53 is formed with a suction hole 81 of a vacuum chuck (fixing device) known in the related art, so that the bottom 37 is sucked with a vacuum pump, not shown, through the suction hole 81 when using the centrifugal blood pump with magnetic coupling 1 to prevent the housing 5 from falling down from the stator 3.

With the configuration of this embodiment as described thus far, when using the centrifugal blood pump with magnetic coupling 1, the housing 5 is fixed to the upper surface of the stator 3 by the vacuum chuck by arranging the housing 5 on the housing mounting base 55, then inserting the bottom 37 between the housing mounting base 55 and the torque transmission disk 15 and operating the vacuum pump.

When the housing 5 is arranged on the upper surface of the stator 3 in this manner, the rotor 7 and the impeller 9 are magnetically floated in the completely non-contact manner with respect to the housing 5 by the magnetic coupling generated between the rotor 7 and the torque transmission disk 15 and the magnetic coupling generated between the electromagnets 17x, 19x, 17y, 19y and the rotor 7, and hence is supported in a non-contact manner.

Then, when the motor 13 is rotated in this state, and the torque transmission disk 15 is rotated in the direction indicated by the arrow (direction Ψ) as shown in FIG. 2 and FIG. 4, the torque is transmitted to the rotor 7 by the magnetic coupling generated between the torque transmission disk 15 and the rotor 7 and hence the rotor 7 is rotated in the same direction and the impeller 9 is rotated in the same direction.

Therefore, blood flowed into the inflow 11 on the top of the housing 5 receives kinetic energy by the rotation of the impeller 9 and flows out from the outflow on the side surface. Then, as described above, the displacement or inclination of the rotor 7 in the direction of thrust (direction Z) and the directions of inclination (direction Θ, direction Φ) is restored to the ideal position by the magnetic coupling 41, 79 when the impeller 9 rotates, and the displacement of the rotor 7 in the radial directions (direction X, direction Y) is restored to the ideal position by the feedback-control of the control device via the magnetic coupling 41, so that the rotor 7 and the impeller 9 rotate stably in the direction Ψ.

In association with driving of the motor 13, the motor 13 generates heat by copper loss and iron loss due to fluctuation of the magnetized direction. However, according to this embodiment, with the structure in which the motor 13 is arranged under the stator 3 apart from the housing 5 as described above, and the power transmitting shaft 63 is formed of a material having low heat conductivity, heat of the motor 13 is not transferred to blood flowing down in the housing and, in addition, the torque transmission disk 15 rotates synchronously with the rotor 7, so that the fluctuation of the magnetized direction does not occur in the vicinity of the housing 5.

Replacement of the blood-contact part including the housing 5 and the rotor 7 and the impeller 9 mounted to the interior thereof is achieved only by removing the housing 5 from the stator 3 and attaching a new housing to the stator 3.

As described thus far, with the structure in which the impeller 9 to be integrated in the housing 5 is supported by the magnetic couplings 41, 79 in a non-contact manner, the centrifugal blood pump with magnetic coupling 1 according to this embodiment has advantages such that the durability is improved and the expiration date for use of the disposable parts is dramatically prolonged in comparison with the related out in which the impeller is supported by a contact-type bearing, and disadvantages in the related art such as plaque formation around the bearing or hemolysis caused by the bearing are solved.

According to this embodiment, with the structure in which the motor 13 is arranged under the stator 3 apart from the housing 5, and the power transmitting shaft 63 is formed of the material having low heat conductivity to prevent heat of the motor 13 from being transferred easily to blood flowing down in the housing 5, coagulation of blood by heat is reliably prevented.

In addition, as described above, when the magnetic soft iron cores 43 of the electromagnets 17x, 19x, 17y, 19y are formed of annealed pure iron, the hysteresis loss of the magnetic coupling 41 is lowered, which contributes to reduction of possibility of heat generation of the electromagnets 17x, 19x, 17y, 19y, so that the coagulation of blood flowing down in the housing 5 is prevented. In contrast, when the magnetic soft iron core 43 is formed of powder core, eddy current loss is reduced, which contributes to reduction of possibility of heat generation of the electromagnets 17x, 19x, 17y, 19y, and the band width of the electromagnetic force emitted from and controlled by the magnetic coupling 41 is expanded. Therefore, vibrations of the rotor 7 are advantageously reduced, which contributes to prevention of hemolysis or plaque formation of blood.

Then, the magnetic resistance of the magnetic circuit is also small, which is advantageous for reduction of power consumption of the magnetic coupling.

Furthermore, in this embodiment, only one neodymium permanent magnet 21 is used for the rotor 7 in the housing 5 as the disposable part, and the rotor 7 by itself is configured only of three parts of neodymium permanent magnet 21 and the two magnetic soft iron rings 23, 25, so that a simpler rotor structure than the related arts disclosed in Non-Patent Documents 1 to 3 is achieved, which advantageously contributes to cost reduction of the disposable part.

In addition, according to this embodiment, the housing 5 as the disposable part is fixed to the stator 3 with the vacuum chuck, the possibility of occurrence of unexpected accident such as coming off of the housing 5 when it is used during cardiac surgery or after the cardiac surgery is avoided.

In the embodiment described above, the vacuum chuck is employed as the fixing device for fixing the housing 5 to the stator 3. However, the housing 5 may be prevented from coming off using friction between the outer peripheral surface of the bottom 37 of the housing 5 and the inner peripheral surface of the housing mounting base 55.

Figure 8:
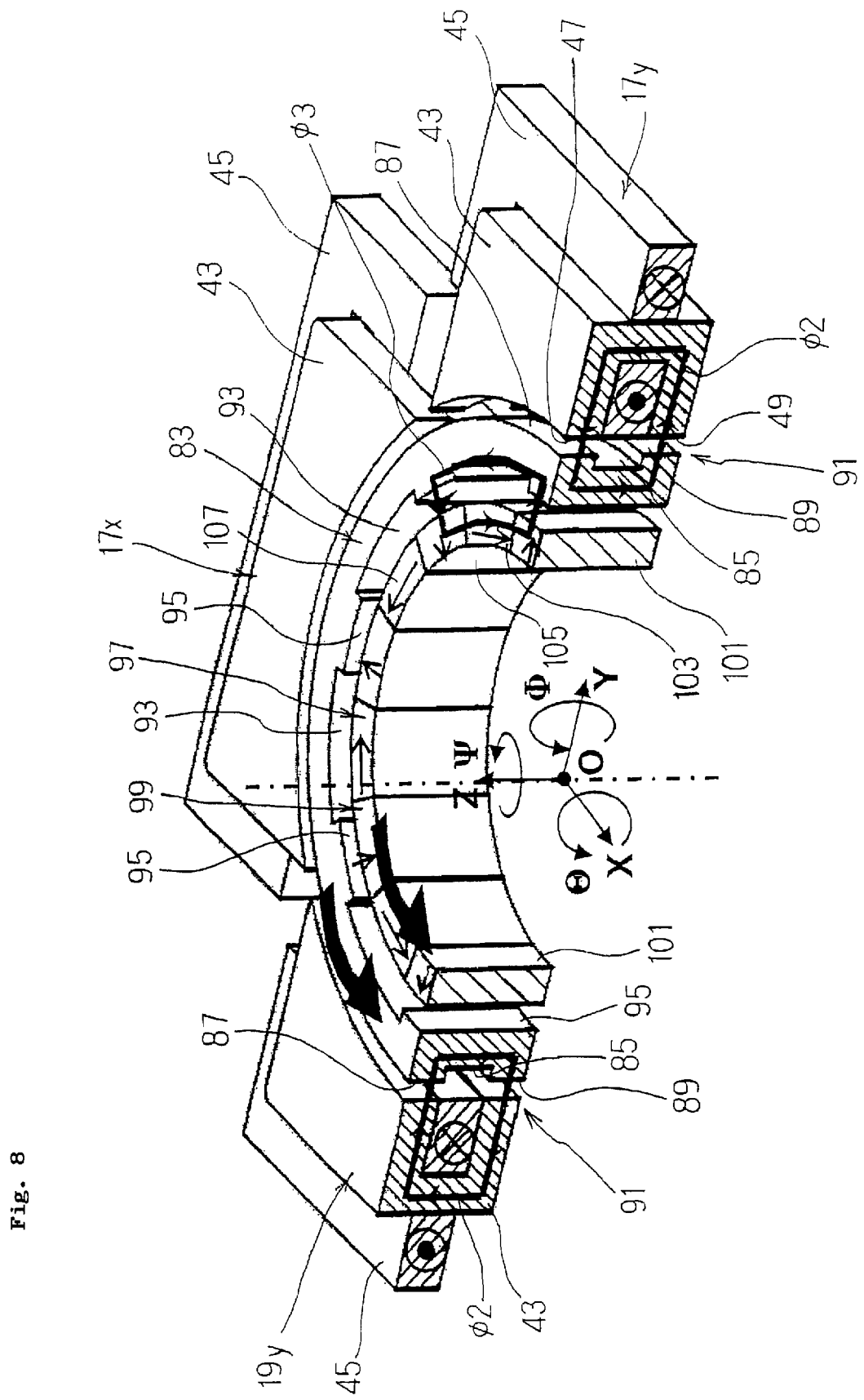
FIG. 8 is an enlarged perspective cross-sectional view of the rotor, the electromagnet and the torque transmission disk of the disposable centrifugal blood pump with magnetic coupling according to another embodiment described in Claim 4 and Claim 5.

FIG. 8 illustrates the structure of a rotor, electromagnets and a torque transmission disk mounted to the centrifugal blood pump with magnetic coupling according to an embodiment stated in Claim 4 and Claim 5. In this embodiment, the rotor and the torque transmission disk have different structures from the rotor 7 and the torque transmission disk 15 described above. Referring now to the drawings, this embodiment will be described.

The configuration other than the rotor and the torque transmission disk is the same as the embodiment shown in FIG. 1, and hence the same parts are designated by the same reference numerals and description thereof is omitted.

In FIG. 8, reference numeral 83 designates an integral type rotor employing a ring-shaped magnetic soft iron ring which is thicker than the magnetic soft iron ring 23 described above, and the impeller 9 is attached to the top thereof via the connecting member 35. These members are stored in the housing 5.

A groove 85 is formed on the outer peripheral surface of the rotor 83 in the circumferential direction, and a ring-shaped pole face 87 is formed so as to oppose the pole faces 47 of the electromagnets 17x, 19x, 17y, 19y on one side thereof. Likewise, a ring-shaped pole face 89 is formed so as to oppose the pole faces 49 of the electromagnets 17x, 19x, 17y, 19y on the other side on the outer peripheral surface of the rotor 83. With the arrangement of the pole faces 87, 89 opposed to the pole faces 47, 49 of the rotor 83, a magnetic coupling which forms a closed loop of magnetic flux $\phi 2$ indicated by an arrow in the drawing is generated between the rotor 83 and the electromagnets 17x, 19x, 17y, 19y.

However, being different from the rotor 7 in FIG. 2, the rotor 83 in this embodiment does not have a permanent magnet for generating magnetic flux, and hence it is necessary to generate a magnetic coupling by applying bias to the electromagnets 17x, 19x, 17y, 19y.

Then, a magnetic coupling 91 formed of this magnetic coupling restores the displacement or inclination of the rotor 83 in the direction of thrust (direction Z) and the directions of inclination (direction $\Theta$, direction $\Phi$) to the ideal position in the same manner as the magnetic coupling 41 described above, and the control device feedback-controls the displacement in the radial directions (direction X, direction Y) to restore the rotor 83 to the ideal position.

On the other hand, the inner peripheral surface of the rotor 83 is formed with eight grooves 93 in the axial direction at regular intervals so that eight teeth-like pole faces 95 are formed so as to project inward.

In this embodiment, a torque transmission disk 97 is configured of a Halbach type permanent magnet array 99 instead of the torque transmission disk 15 described above.

The permanent magnet array 99 shown in the drawing includes four types of permanent magnets 101, 103, 105, 107, whose directions of magnetization are shifted by 90°, arranged along the circumferential direction repeatedly in sequence (16 pieces in total).

Then, the pole faces 95 of the rotor 83 are arranged so as to oppose the permanent magnets 101, 105 which are magnetized inwardly and outwardly in the radial direction of the torque transmission disk 97. In this configuration, a magnetic coupling which forms a closed loop of magnetic flux $\phi 3$ indicated by an arrow extending in parallel to the radial directions (direction X, direction Y) is generated between the torque transmission disk 97 and the rotor 83, so that the torque of the motor 13 is transmitted form the torque transmission disk 97 to the rotor 83 by the magnetic coupling.

As in the case of the torque transmission disk 15 shown in FIG. 1, the torque transmission disk 97 is connected to the distal end of the power transmitting shaft 63 via the connecting member 67.

Therefore, according to this embodiment, the desired object is achieved as in the case of the centrifugal blood pump with magnetic coupling 1 shown in FIG. 1. However, according to this embodiment, it is not necessary to use the permanent magnet for the rotor 83 as the disposable part, and hence the structure of the rotor 83 is simpler than the rotor 7 described above, and hence further cost reduction is advantageously achieved.

The rotor 83 may be used in the centrifugal blood pump with magnetic coupling 1 in FIG. 1 instead of the rotor 7 in FIG. 2.

As described above, the teeth-shaped pole faces 95 are formed on the inner peripheral surface of the rotor 83 so as to project inward at regular intervals in this embodiment as well. However, the pole faces 95 do not necessarily have to be provided at regular intervals and, for example, the four pole faces 95 may be formed at intervals of 100° and 80° in line symmetry so as to project therefrom.

Figure 9:
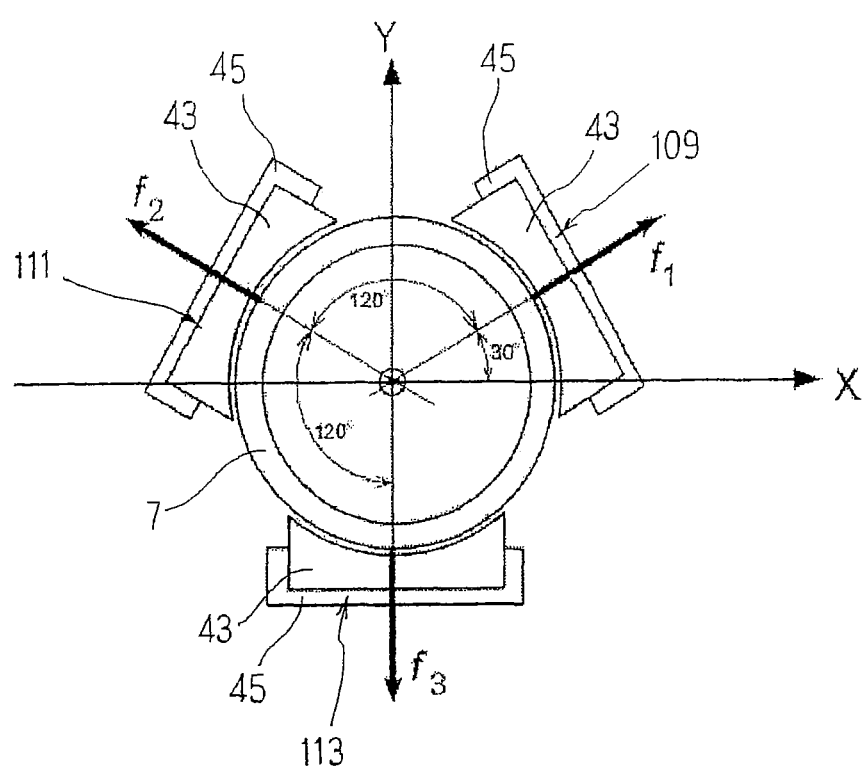
FIG. 9 is a plan view of the rotor and the electromagnet of the centrifugal blood pump with magnetic coupling according to a second embodiment described in Claim 1 to Claim 3.

FIG. 9 shows a second embodiment of the centrifugal blood pump with magnetic coupling according to Claim 1 to Claim 3, and in the embodiment shown in FIG. 1 to FIG. 6, the four electromagnets 17x, 19x, 17y, 19y are arranged around the rotor 7 (housing 5) at the intervals of 90°. However, three electromagnets 109, 111, 113 having the same structure as the electromagnet 17y may be arranged around the rotor 7 (housing 5) at regular intervals of 120° as shown in FIG. 9.

According to this embodiment, there are infinite numbers of combination as methods of power supply to the coils 45 of the respective electromagnets 109, 111, 113. As an example, by providing an electric current ix to the electromagnet 109 and providing an electric current –ix in the opposite direction to the electromagnet 111, a drive force only in the direction X is generated.

The configuration of other parts is the same as the embodiment shown in FIG. 1, and hence description thereof will be omitted.

In this manner, according to this embodiment as well, the desired object is achieved as the first embodiment shown in FIG. 1, and the number of electromagnets may advantageously be reduced to further simplify the structure.

The structure of this embodiment may also be applied to the embodiment shown in FIG. 8.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents may be resorted to, falling within the scope thereof.

What is claimed is:

1. A disposable centrifugal blood pump with magnetic coupling comprising:
   a disposable housing including a top surface, a side surface and a bottom with an inflow at the top surface and an outflow at the side surface; and
   a stator detachably connected to the housing,
   wherein the housing includes:
   a cylindrical rotor being formed of magnetic material and including an outer peripheral surface and inner peripheral surface; and
   an impeller integrated to the rotor,
   wherein the cylindrical rotor includes ring-shaped pole faces extending along a circumferential direction of the outer peripheral surface thereof and a plurality of pole faces projecting inward from the inner peripheral surface
   wherein said stator includes:
   three or more electromagnets for electromagnetic coupling, the three or more electromagnets being arranged around the housing at regular intervals and having pole faces opposed to the pole faces projected of the outer peripheral surface of the rotor, the electromagnets to generate a magnetic coupling between the stator and the rotor;
   a torque transmission disk being formed by sandwiching a ring-shaped permanent magnet magnetized in an axial direction between an upper ring member and a lower ring member, the upper ring member and the lower ring member including a magnetic material and having a plurality of pole faces corresponding to the pole faces at the inner peripheral surface of the rotor for generating a magnetic coupling between the torque transmission disk and the rotor;
   a motor arranged apart from said housing for rotating the torque transmission disk; and
   wherein the bottom of the housing includes a cylindrical shape along a contour shape of the rotor and detachably attached between said electromagnets and the torque transmission disk.

2. The disposable centrifugal blood pump with magnetic coupling according to claim 1, wherein the rotor is formed by sandwiching one ring-shaped permanent magnet magnetized in an axial direction between an upper ring member and a lower ring member, the upper and lower ring members being formed of magnetic material and formed with teeth in the axial direction on an inner peripheral surface thereof, and the permanent magnet of the torque transmission disk is magnetized in a direction opposite from the permanent magnet of the rotor.

3. The disposable centrifugal blood pump with magnetic coupling according to claim 2, wherein the housing is fixed to the stator via a fixing device.

4. The disposable centrifugal blood pump with magnetic coupling according to claim 1, wherein the housing is fixed to the stator via a fixing device.

5. The blood pump of claim 1, wherein the torque transmission disk comprises a Halbach type permanent magnet array.

6. The blood pump of claim 5, comprising a displacement gauge for measuring displacement of the rotor in the radial direction.

7. A disposable centrifugal blood pump with magnetic coupling comprising:
   a disposable housing;
   a reusable stator detachably attached to the housing,
   wherein the housing includes:
   a cylindrical rotor including ring-shaped pole faces extending along a circumferential direction of an outer peripheral surface thereof and including a plurality of pole faces projecting inward from an inner peripheral surface thereof; and
   an impeller attached to the rotor, wherein
   said stator includes:
   three or more electromagnets for electromagnetic coupling, the three or more electromagnets being arranged around the housing at regular intervals and having pole faces opposed to the pole faces projected from the outer peripheral surface of the rotor, the electromagnets generating a magnetic coupling between the stator and the rotor;
   a torque transmission disk including sandwiched ring members and a plurality of pole faces corresponding to the pole faces at an inner peripheral surface of the cylindrical rotor;
   a motor arranged apart from said housing for rotating the torque transmission disk; and
   wherein the bottom of the housing is formed into a cylindrical shape along a contour shape of the rotor and detachably attached between said stator electromagnets and the torque transmission disk.

8. The blood pump of claim 7, wherein the torque transmission disk comprises a Halbach type permanent magnet array including a row of permanent magnets whose directions of magnetization are shifted by 90° for generating a magnetic coupling between the stator and the pole faces formed on an inner peripheral surface of the rotor so as to oppose the permanent magnets magnetized inwardly and outwardly in the radial direction.

9. The blood pump of claim 7, comprising a displacement gauge for measuring displacement of the rotor in the radial direction.

10. A blood pump comprising:
    a disposable housing, and
    a reusable component, said reusable component comprising a stator and a motor;
    wherein said housing includes a top surface, a side surface and a bottom with an inflow at the top surface, and an outflow at the side surface; and
    wherein said housing comprises a rotor and an impeller attached to the rotor;
    said rotor comprising: a ring-shaped permanent magnet, an upper magnetic ring member and a lower magnetic ring member, wherein the upper magnetic ring member and the lower magnetic ring member have an inner peripheral surface and an outer peripheral surface, and wherein the permanent magnet is between the upper magnetic ring member and lower magnetic ring member, wherein the outer peripheral surface of the lower magnetic ring member and the outer peripheral surface of the upper magnetic ring member define a plurality of outer pole faces along the external circumference of the rotor; and wherein the inner peripheral surface of the lower magnetic ring member and the inner peripheral surface of the upper magnetic ring member define a plurality of inner pole faces along the internal circumference of the rotor;
    said bottom of housing is formed into a shape in accordance with the cylindrical shape of the rotor;
    said stator comprising:
    three or more electromagnets for electromagnetic coupling, the three or more electromagnets being arranged around said housing at regular intervals and having a plurality of pole faces magnetically opposed to said outer pole faces along the external circumference of the rotor, wherein said electromagnets generate a magnetic coupling between the stator and the rotor; and a torque transmission disk comprising a ring-shaped permanent magnet magnetized in an axial direction, an upper magnetic ring member and a lower magnetic ring member, wherein the permanent magnet is between the upper magnetic ring member and the lower magnetic ring member, and wherein the permanent magnet, the upper magnetic ring member and the lower magnetic ring member of the torque transmission disk generate a magnetic coupling between the torque transmission disk and the rotor.

11. The blood pump of claim 10, comprising a displacement gauge for measuring displacement of the rotor in the radial direction.

12. The blood pump of claim 11, wherein said motor is arranged apart from said housing and is to rotate said torque transmission disk.

13. The blood pump of claim 12, wherein said bottom of housing is detachably attached between the stator electromagnets and the torque transmission disk.

14. The blood pump of claim 10, wherein said motor is arranged apart from said housing and is to rotate said torque transmission disk.

15. The blood pump of claim 10, wherein said bottom of housing is detachably attached between the stator electromagnets and the torque transmission disk.

16. The blood pump of claim 10, further comprising a gauge to measure displacement of the rotor in the radial direction.

17. The blood pump of claim 16, wherein said gauge includes a displacement gauge.

18. The blood pump of claim 17, wherein the ring-shaped permanent magnet of the rotor is magnetized in an axial direction, and wherein the upper ring member is formed with teeth in the axial direction on its inner peripheral surface, and the lower ring member is formed with teeth in the axial direction on its inner peripheral surface, and the permanent magnet of the torque transmission disk has a plurality of pole faces, wherein said pole faces of said permanent magnet of the torque transmission disk are magnetized in the direction opposite of the permanent magnet of the rotor.

19. The blood pump of claim 10, wherein the ring-shaped permanent magnet of the rotor is magnetized in an axial direction, and wherein the upper ring member is formed with teeth in the axial direction on its inner peripheral surface, and the lower ring member is formed with teeth in the axial direction on its inner peripheral surface, and the permanent magnet of the torque transmission disk has a plurality of pole faces, wherein said pole faces of said permanent magnet of the torque transmission disk are magnetized in the direction opposite of the permanent magnet of the rotor.

* * * * *